(12) United States Patent
Kassab

(10) Patent No.: US 10,238,311 B2
(45) Date of Patent: Mar. 26, 2019

(54) DEVICES, SYSTEMS, AND METHODS TO EVALUATE CARDIOVASCULAR FUNCTION

(75) Inventor: Ghassan S. Kassab, Zionsville, IN (US)

(73) Assignee: CVDevices, LLC, San Diego, CA (US)

(*) Notice: Subject to any disclaimer, the term of this patent is extended or adjusted under 35 U.S.C. 154(b) by 1975 days.

(21) Appl. No.: 12/521,258

(22) PCT Filed: Jan. 22, 2008

(86) PCT No.: PCT/US2008/000739
§ 371 (c)(1),
(2), (4) Date: Jun. 25, 2009

(87) PCT Pub. No.: WO2008/091557
PCT Pub. Date: Jul. 31, 2008

(65) Prior Publication Data
US 2010/0030055 A1   Feb. 4, 2010

Related U.S. Application Data

(60) Provisional application No. 60/881,841, filed on Jan. 23, 2007.

(51) Int. Cl.
*A61B 5/053*   (2006.01)

(52) U.S. Cl.
CPC ............ *A61B 5/053* (2013.01); *A61B 5/0538* (2013.01)

(58) Field of Classification Search
CPC ....... A61B 5/024; A61B 5/0205; A61B 5/053; A61B 5/0538; A61B 5/0215; A61B 5/0245
USPC .......................................... 600/508; 607/4-5
See application file for complete search history.

(56) References Cited

U.S. PATENT DOCUMENTS

| | | | | |
|---|---|---|---|---|
| 4,562,843 A | * | 1/1986 | Djordjevich | A61B 5/0205 600/485 |
| 4,840,182 A | * | 6/1989 | Carlson | A61B 5/0535 600/505 |
| 7,454,244 B2 | | 11/2008 | Kassab et al. | |
| 2002/0045810 A1 | | 4/2002 | Ben-Haim | |
| 2004/0024329 A1 | * | 2/2004 | Jansen | A61B 5/0275 600/526 |
| 2005/0203434 A1 | | 9/2005 | Kassab | |
| 2007/0016007 A1 | | 1/2007 | Govari et al. | |

(Continued)

FOREIGN PATENT DOCUMENTS

WO   WO 08/10905   1/2008

OTHER PUBLICATIONS

PCT/US08/00739, PCT Search Report and Written Opinion, dated Jul. 11, 2008.

*Primary Examiner* — Michael Kahelin
*Assistant Examiner* — Minh Duc Pham
(74) *Attorney, Agent, or Firm* — Reichel Stohry LLP; Mark C. Reichel; Natalie J. Dean

(57) ABSTRACT

Devices and methods are disclosed which relate to the detection of cardiovascular efficiency and risk of disease. The rate of volumetric change of the heart can be determined by measuring the parallel conductance across electrodes attached to the heart. Measurements from a lumen would consider the total conductance. The rate of volumetric or lumen cross-section area change can then be compared to an average model to determine the health of a patient.

17 Claims, 9 Drawing Sheets

(56) References Cited

U.S. PATENT DOCUMENTS

2007/0066905 A1* 3/2007 Zhang ................. A61N 1/3627
600/509
2009/0210020 A1* 8/2009 Feldman .............. A61B 5/0215
607/4

* cited by examiner

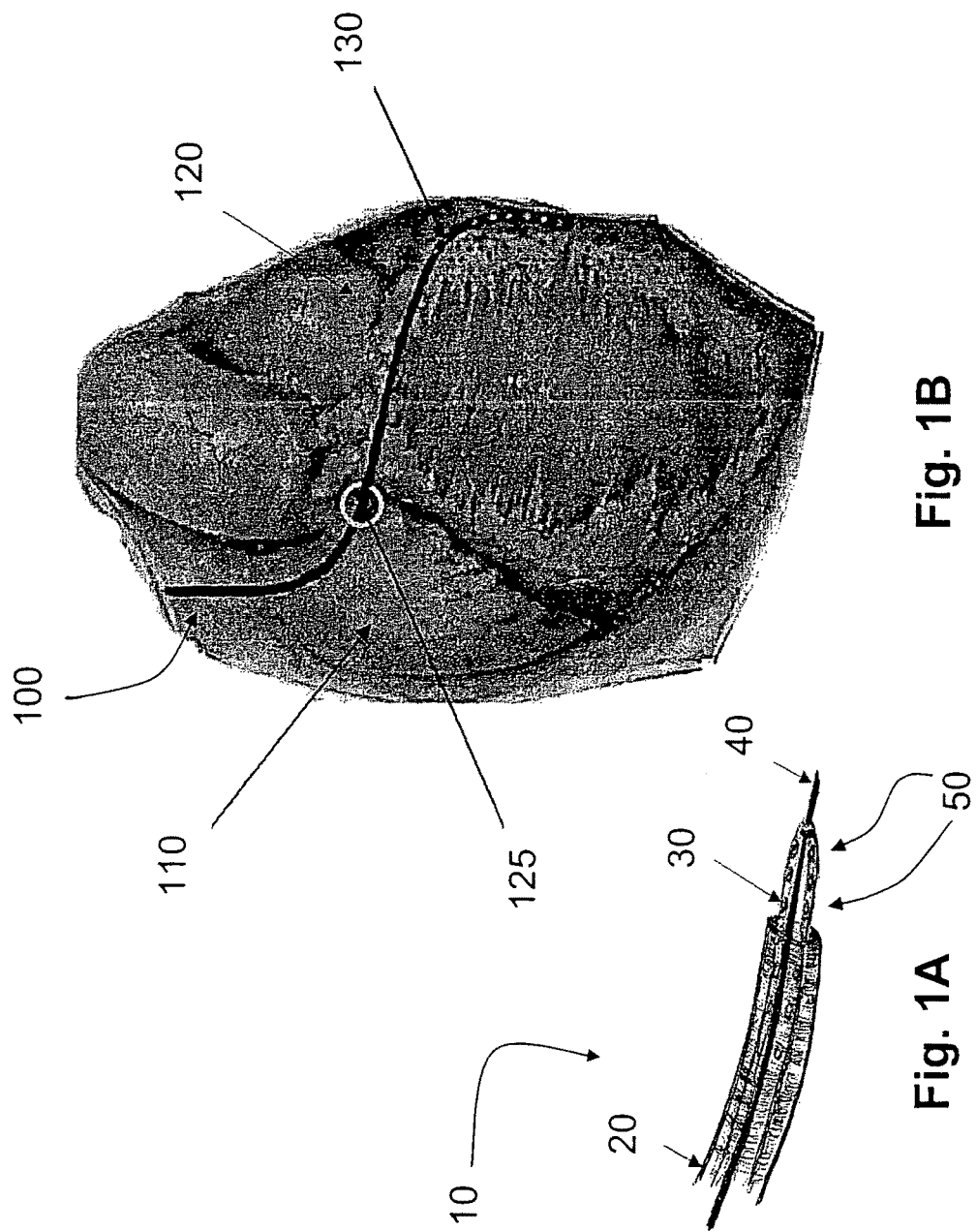

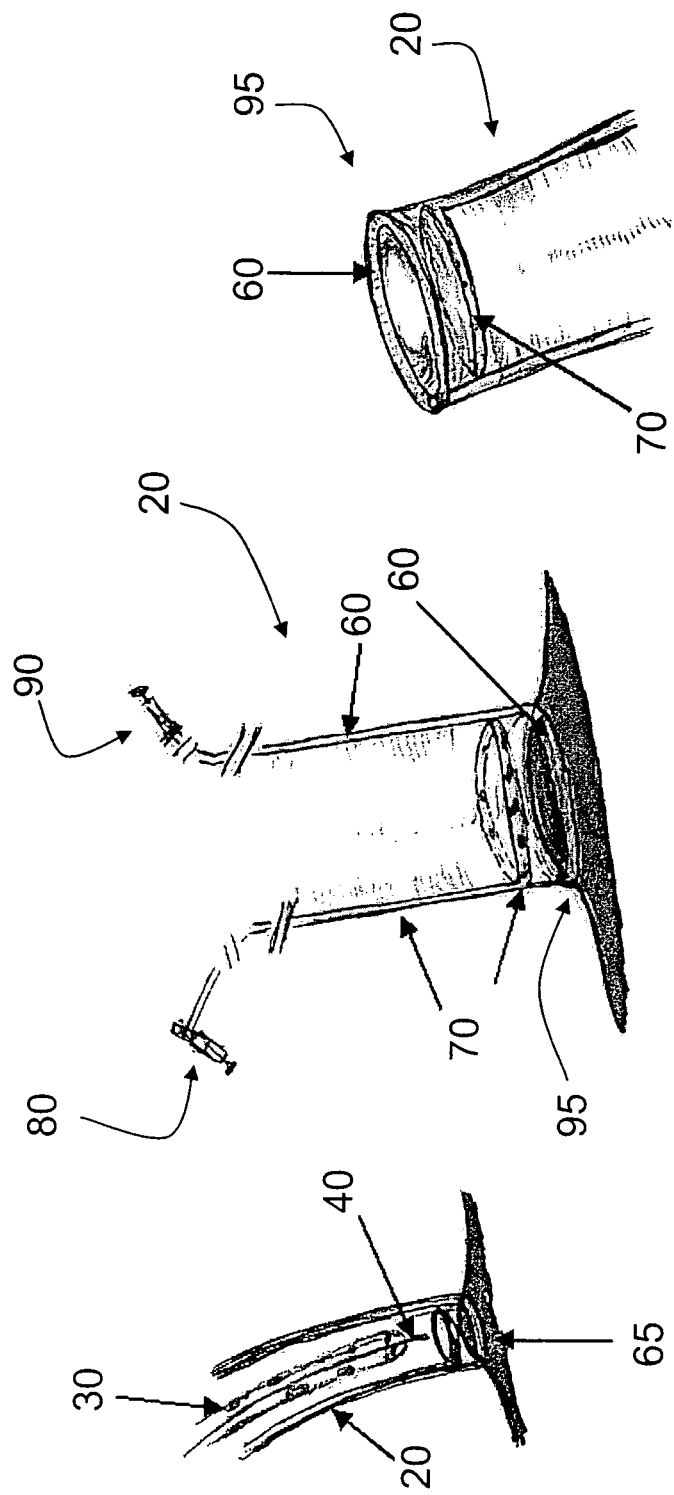

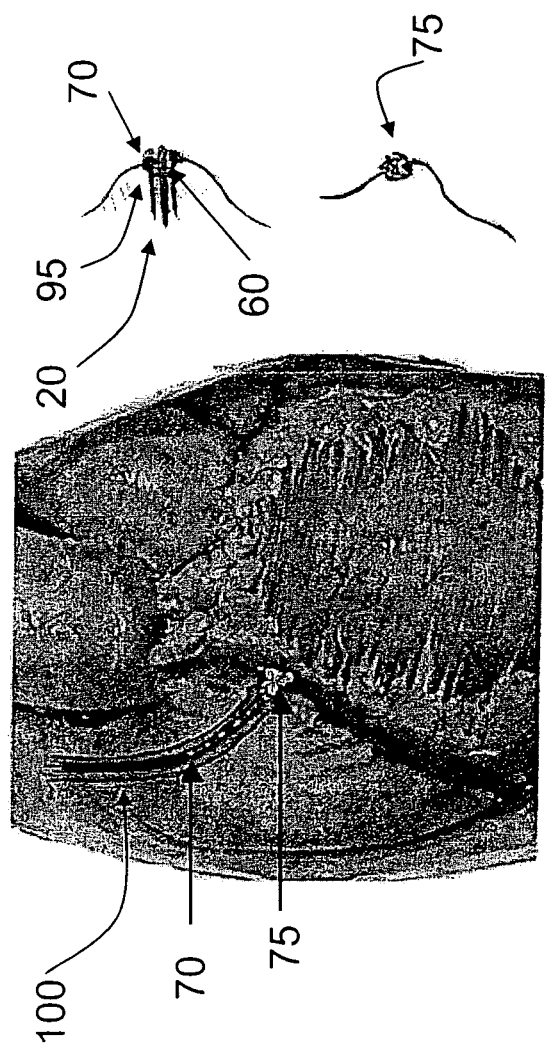

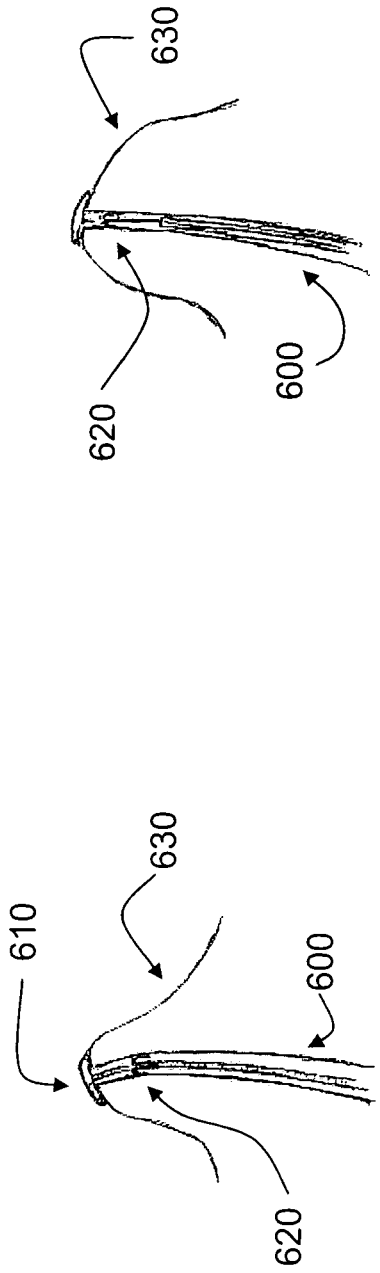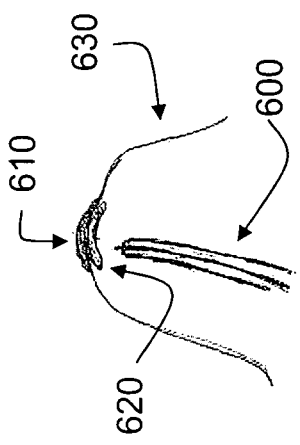
Fig. 4A
Fig. 4C
Fig. 4B

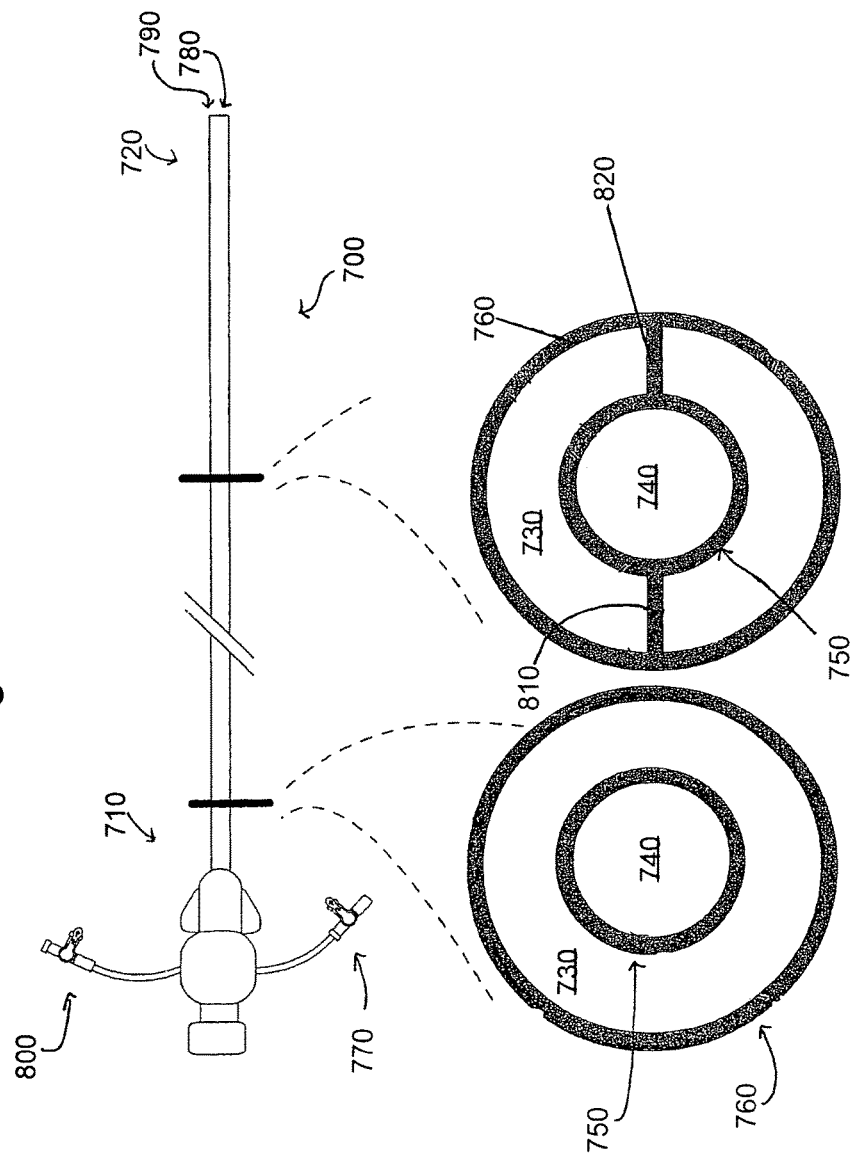

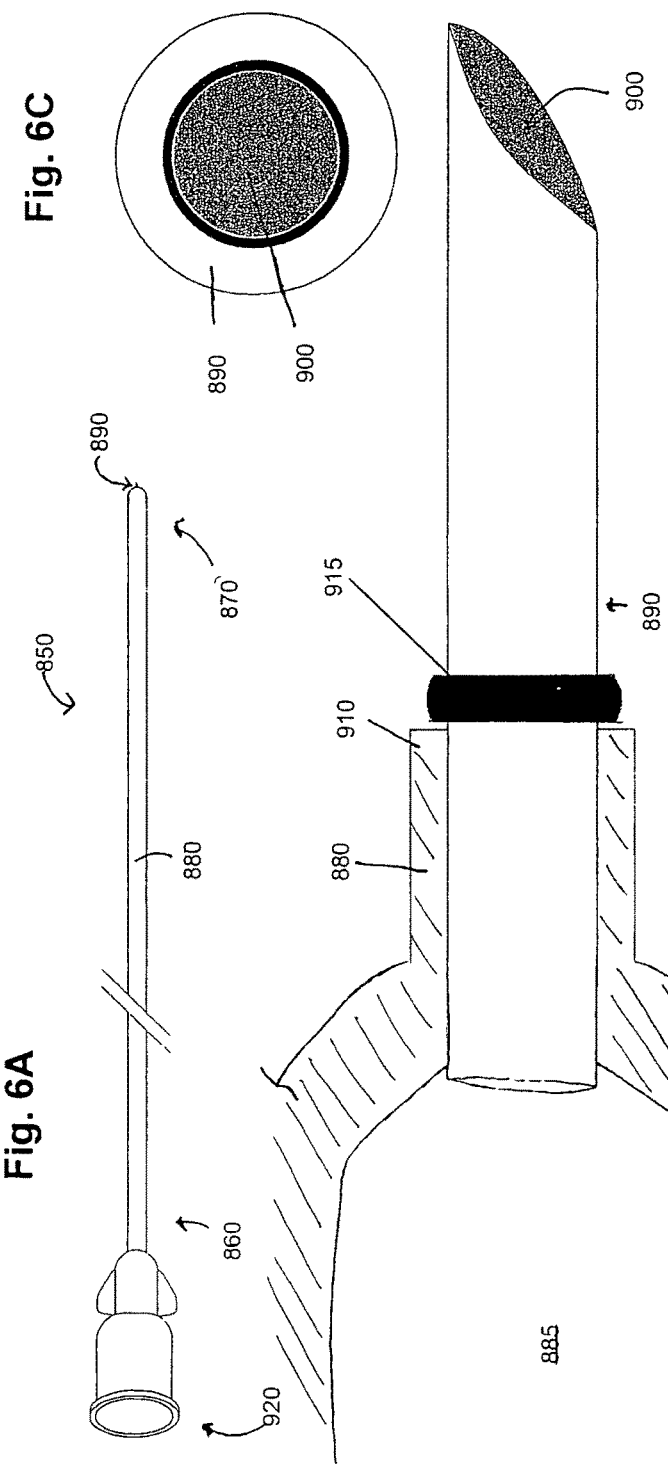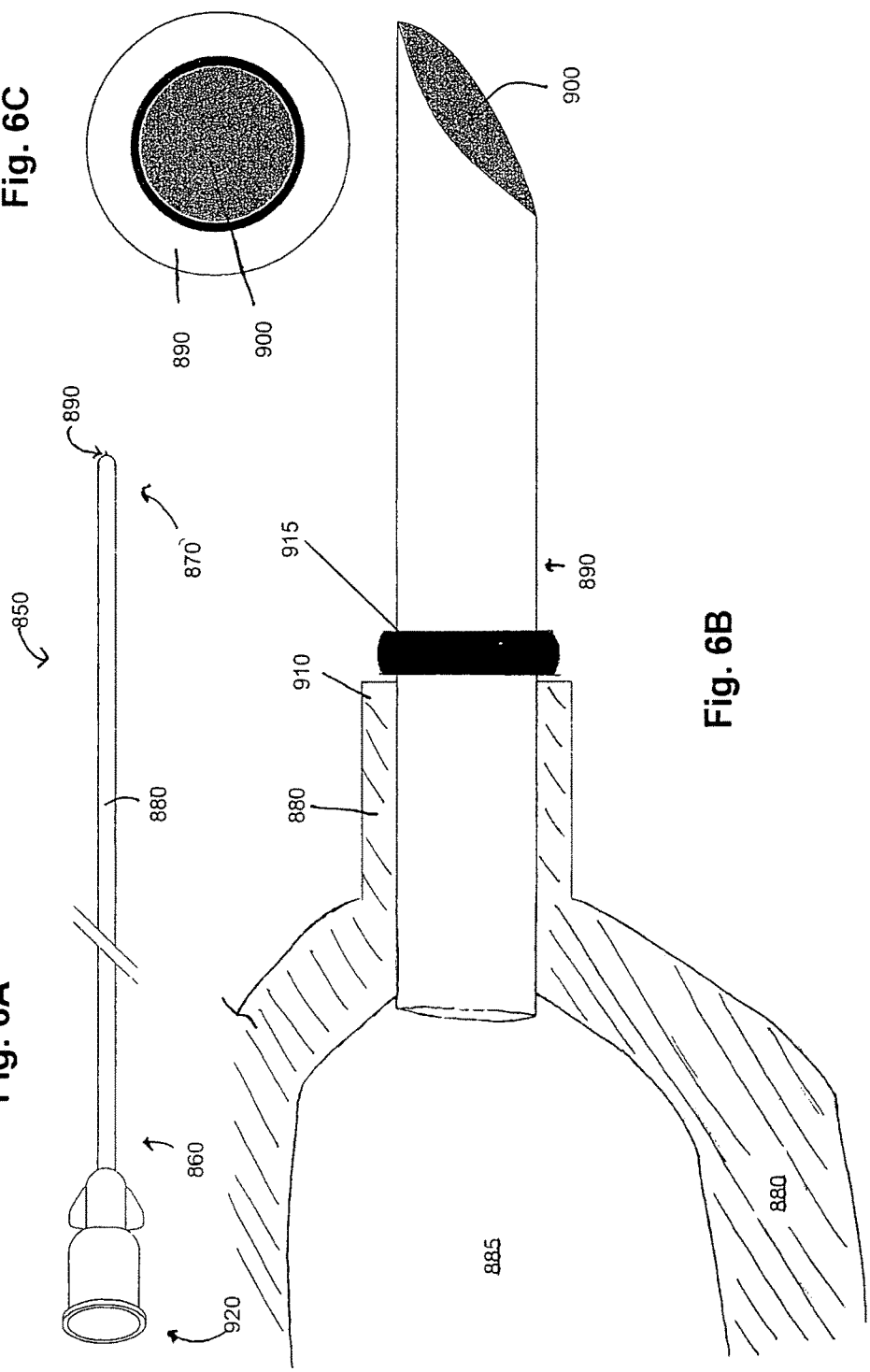

DEVICES, SYSTEMS, AND METHODS TO EVALUATE CARDIOVASCULAR FUNCTION

PRIORITY

The present application is related to, and claims the priority benefit of, International Patent Application Serial No. PCT/US2008/000739, filed Jan. 22, 2008, which is related to, and claims the priority benefit of, U.S. Provisional Patent Application Ser. No. 60/881,841, filed Jan. 23, 2007. The contents of each of these applications are hereby incorporated by reference in their entirety into this disclosure.

BACKGROUND

The disclosure of the present application relates generally to vessel and heart efficiency and risk of disease. More particularly, the disclosure of the present application relates to techniques for evaluating cardiovascular function.

Many cardiovascular diseases, including diabetes, hypertension, and heart failure, have impaired arterial vasoactivity, namely vasoconstriction and vasodilation. Hypertension, for example, is associated with changes in vasomotor tone and typically attenuates vasodilation. The vasoactivity may also be altered under physiological conditions, such as in normal growth, exercise, etc. The regulation of the vasomotor tone in medium-sized arteries is of particular interest because of the clinical relevance to vasospasm and atherosclerosis.

In addition to the active component (vasoactivity) of blood vessels, there is great interest in the elasticity of vessels. One of the reasons for the great interest stems from the observation that increased stiffness of large elastic arteries represents an early risk factor for cardiovascular diseases. Specifically, increased aortic stiffness is associated with aging, hypertension, diabetes, hyperlipidemia, atherosclerosis, heart failure, and smoking. Furthermore, arterial stiffness has also been shown to be an independent risk factor for cardiovascular events such as primary coronary events, stroke, and mortality. Therefore, the assessment of the passive and active mechanical properties of vessels is particularly important for understanding the mechanisms of cardiovascular disease.

Clinically, the compliance or stiffness of blood vessels is used as an index of vascular mechanics, and hence, vessel function. These measurements can be made from imaging (e.g., ultrasound) to obtain the deformation (change of dimension) and loading (pressure). The endothelial function is typically measured by the degree of vasodilation or reactive hyperemia (namely the change of diameter from imaging) post cuff occlusion. Unfortunately, these measurements can be quite variable and the theoretical basis for the measurements is not well founded. Hence, there is a need to determine a theoretically-based parameter that quantifies the function of blood vessels.

Regarding the heart, much effort has gone into quantifying myocardial function, independent of ventricular loading conditions. In the left ventricle (LV), the peak first time-derivative of LV intracavitary pressure, $dP/dt_{max}$, is a sensitive cardiac index of inotropicity and the current detection 'gold standard.' Currently, the ability to obtain an accurate determination of $dP/dt_{max}$ requires measurement of intraventricular LV pressure using invasive cardiac catheterization. In general, it is very difficult to accurately assess ventricular pressure non-invasively.

An additional difficulty with LV $dP/dt_{max}$ is that it is not preload-independent. Conceivably, LV pressure-volume relationship and elastance reflect LV contractile function more accurately formalized as the time-varying elastance of the ventricle, by defining elastance, E. Elastance is defined as $E(t)=P(t)/(V(t)-V_d)$, where P(t) and V(t) are ventricular pressure and volume that vary with time (t), respectively. $V_d$ is the LV volume corresponding to zero LV pressure obtained by drawing a tangent to the pressure-volume curves at the end-ejection.

It has been shown that the end-systolic pressure volume (ESPV) relationship, which is the loci of pressure and volume points at end-systole, is insensitive to variations of both the end-diastolic volume (preload) and the mean arterial pressure (afterload). The ESPV relationship is usually a straight line with a slope of $E_{es}$. It is found that $E_{es}$ remains essentially constant if the preload and afterload are allowed to vary within the physiologic range, but is sensitive to inotropic agents and ischemia. Hence, $E_{es}$ has been proposed as a "load independent" index of contractility of the ventricle. Elastance measures also require cardiac catheterization for measurement of pressure which further reduces their clinical utility. An additional limitation of $E_{es}$ is that it is not easy to change afterload and obtain multiple pressure-volume data points in a given subject while maintaining a constant contractility. As such, it is impractical to use $E_{es}$ clinically for patient-specific LV catheterization-ventriculography data. Hence, there is a need for a cardiac index that is more readily accessible and practical.

SUMMARY

The disclosure of the present application measures an index of vessel and heart function to evaluate the efficiency of the cardiovascular system and risk of disease. The measurements are taken with an impedance catheter. The catheter may be inserted into the lumen of the vessel or heart chamber. Alternatively, the catheter may be inserted into the pericardial space or directly placed on the heart as during open heart surgery. A patch containing the excitation and detection electrodes can be made to adhere to the surface through glue that is introduced through the lumen of the catheter into pores of the patch if the percutaneous approach is used. Alternatively, the patch may be glued on by hand with the open surgery approach. The electrodes are then interfaced with an impedance module to measure voltage differences. The voltage differences are then either compared to an average model, or combined with other measurements to create an average model.

In at least one embodiment of a device for determining the index of a heart and/or vessel function according to the present disclosure, the device comprises an impedance catheter comprising a patch, the patch comprising a first excitation electrode, a second excitation electrode, a first detection electrode, and a second detection electrode, and a conductance reader in connection with the catheter, the conductance reader operable to detect conductance from the first detection electrode and the second detection electrode, whereby an assessment of the index of a heart and/or vessel function may be determined based upon the conductance detected from the first detection electrode and the second detection electrode. In another embodiment, the conductance reader comprises a data acquisition and processing system. In yet another embodiment, the data acquisition and processing system comprises a processor, a storage medium operably connected to the processor, the storage medium capable of receiving and storing conductance data, and a program stored upon the storage medium, the program operable by the processor upon the conductance data to compare the conductance data to a rate of volumetric change of a heart and/or vessel.

In at least one embodiment of a device for determining the index of a heart and/or vessel function according to the present disclosure, the processor compares the conductance data from conductance acquired from the epicardial surface of a heart. In another embodiment, the processor compares the conductance data from conductance acquired from the lumen surface of a heart. In yet another embodiment, the conductance reader comprises a parallel conductance reader, and wherein the parallel conductance reader is operable to detect parallel conductance. In an additional embodiment, the parallel conductance reader comprises a data acquisition and processing system. In another embodiment, the data acquisition and processing system comprises a processor, a storage medium operably connected to the processor, the storage medium capable of receiving and storing parallel conductance data, and a program stored upon the storage medium, the program operable by the processor upon the parallel conductance data to compare the parallel conductance data to a rate of volumetric change of a heart and/or vessel.

In at least one embodiment of a device according to the present disclosure, the processor compares the parallel conductance data from parallel conductance acquired from the epicardial surface of a heart. In a further embodiment, the processor compares the parallel conductance data from parallel conductance acquired from the lumen surface of a heart. In another embodiment, the patch is positioned upon the epicardial surface of a heart, and wherein the conductance reader is operable to detect conductance from the epicardial surface of the heart. In yet another embodiment, the patch is positioned upon the lumen surface of a heart, and wherein the conductance reader is operable to detect conductance from the lumen surface of the heart. In an additional embodiment, the patch is positioned upon the epicardial surface of a heart, and wherein the parallel conductance reader is operable to detect parallel conductance from the epicardial surface of the heart.

In at least one embodiment of a device for determining the index of a heart and/or vessel function according to the present disclosure, the patch is positioned upon the lumen surface of a heart, and wherein the parallel conductance reader is operable to detect parallel conductance from the lumen surface of the heart. In another embodiment, the processor is operable to evaluate the maximum rate of volumetric change of the heart. In yet another embodiment, the processor is operable to evaluate the maximum rate of volumetric change of the heart. In an additional embodiment, the wherein the processor compares the conductance data from conductance acquired from the outer surface of a vessel.

In at least one embodiment of a device for determining the index of a heart and/or vessel function according to the present disclosure, the processor compares the conductance data from conductance acquired from the lumen surface of a vessel. In another embodiment, the processor compares the parallel conductance data from parallel conductance acquired from the outer surface of a vessel. In yet another embodiment, the processor compares the parallel conductance data from parallel conductance acquired from the lumen surface of a vessel. In an additional embodiment, the patch is positioned upon the epicardial surface of a vessel, and wherein the conductance reader is operable to detect conductance from the epicardial surface of the vessel.

In at least one embodiment of a device for determining the index of a heart and/or vessel function according to the present disclosure, the patch is positioned upon the lumen surface of a vessel, and wherein the conductance reader is operable to detect conductance from the lumen surface of the vessel. In another embodiment, the patch is positioned upon the epicardial surface of a vessel, and wherein the parallel conductance reader is operable to detect parallel conductance from the epicardial surface of the vessel. In yet another embodiment, the patch is positioned upon the lumen surface of a vessel, and wherein the parallel conductance reader is operable to detect parallel conductance from the lumen surface of the vessel. In an additional embodiment, the processor is operable to evaluate the maximum rate of lumen cross-sectional area change of a vessel. In a further embodiment, the processor is operable to evaluate the maximum rate of lumen cross-sectional area change of a vessel.

In at least one embodiment of a device for determining the index of a heart and/or vessel function according to the present disclosure, the device further comprises a current source, the current source operable to provide a supply of electrical current to the first excitation electrode and the second excitation electrode to facilitate the detection of conductance from the first detection electrode and the second detection electrode. In another embodiment, the device further comprises a current source, the current source operable to provide a supply of electrical current to the first excitation electrode and the second excitation electrode to facilitate the detection of parallel conductance from the first detection electrode and the second detection electrode. In yet another embodiment, the first excitation electrode, the second excitation electrode, the first detection electrode, and the second detection electrode each comprise a wire, and wherein each wire is insulated from the other wires.

In at least one embodiment of a device for determining the index of a heart and/or vessel function according to the present disclosure, the device comprises an impedance catheter comprising a patch, the patch comprising a first excitation electrode, a second excitation electrode, a first detection electrode, and a second detection electrode, and a conductance reader in connection with the catheter, the conductance reader operable to detect conductance from the first detection electrode and the second detection electrode, wherein the conductance reader comprises a data acquisition and processing system comprising a processor, a storage medium operably connected to the processor, the storage medium capable of receiving and storing conductance data, and a program stored upon the storage medium, the program operable by the processor upon the conductance data to compare the conductance data to a rate of volumetric change of a heart and/or vessel, whereby an assessment of the index of a heart and/or vessel function may be determined based upon the conductance detected from the first detection electrode and the second detection electrode.

In at least one embodiment of a device for determining the index of a heart and/or vessel function according to the present disclosure, the device comprises an impedance catheter comprising a patch, the patch comprising a first excitation electrode, a second excitation electrode, a first detection electrode, and a second detection electrode, and a parallel conductance reader in connection with the catheter, the parallel conductance reader operable to detect parallel conductance from the first detection electrode and the second detection electrode, wherein the parallel conductance reader comprises a data acquisition and processing system comprising a processor, a storage medium operably connected to the processor, the storage medium capable of receiving and storing parallel conductance data, and a program stored upon the storage medium, the program operable by the processor upon the parallel conductance data to compare the parallel conductance data to a rate of volumetric change of a heart and/or vessel, whereby an assessment of the index of a heart and/or vessel function may be determined based upon the parallel conductance detected from the first detection electrode and the second detection electrode.

In at least one embodiment of a system for determining the index of a heart and/or vessel function according to the present disclosure, the system comprises an impedance catheter assembly, the impedance catheter assembly comprising a catheter, the catheter comprising a patch, and a conductance reader in connection with the catheter assembly, the conductance reader operable to detect conductance from the impedance catheter assembly, whereby an assessment of the index of a heart and/or vessel function may be determined based upon the conductance detected from the catheter assembly. In another embodiment, the patch comprises a first excitation electrode, a second excitation electrode, a first detection electrode, and a second detection electrode. In yet another embodiment, the conductance reader is operable to detect conductance from the first detection electrode and the second detection electrode, and whereby the assessment of the index of a heart and/or vessel function may be determined based upon the conductance detected from the first detection electrode and the second detection electrode.

In at least one embodiment of a system according to the present disclosure, the conductance reader comprises a data acquisition and processing system. In another embodiment, the data acquisition and processing system comprises a processor, a storage medium operably connected to the processor, the storage medium capable of receiving and storing conductance data, and a program stored upon the storage medium, the program operable by the processor upon the conductance data to compare the conductance data to a rate of volumetric change of a heart and/or vessel. In an additional embodiment, the processor compares the conductance data from conductance acquired from the epicardial surface of a heart. In a further embodiment, the processor compares the conductance data from conductance acquired from the lumen surface of a heart.

In at least one embodiment of a system for determining the index of a heart and/or vessel function according to the present disclosure, the conductance reader comprises a parallel conductance reader, and wherein the parallel conductance reader is operable to detect parallel conductance. In another embodiment, the parallel conductance reader comprises a data acquisition and processing system. In yet another embodiment, the data acquisition and processing system comprises a processor, a storage medium operably connected to the processor, the storage medium capable of receiving and storing parallel conductance data, and a program stored upon the storage medium, the program operable by the processor upon the parallel conductance data to compare the parallel conductance data to a rate of volumetric change of a heart and/or vessel. In an additional embodiment, the processor compares the parallel conductance data from parallel conductance acquired from the epicardial surface of a heart. In yet an additional embodiment, the processor compares the parallel conductance data from parallel conductance acquired from the lumen surface of a heart.

In at least one embodiment of a system for determining the index of a heart and/or vessel function according to the present disclosure, the patch is positioned upon the epicardial surface of a heart, and wherein the conductance reader is operable to detect conductance from the epicardial surface of the heart. In another embodiment, the patch is positioned upon the lumen surface of a heart, and wherein the conductance reader is operable to detect conductance from the lumen surface of the heart. In even another embodiment, the patch is positioned upon the epicardial surface of a heart, and wherein the parallel conductance reader is operable to detect parallel conductance from the epicardial surface of the heart. In yet another embodiment, the patch is positioned upon the lumen surface of a heart, and wherein the parallel conductance reader is operable to detect parallel conductance from the lumen surface of the heart.

In at least one embodiment of a system for determining the index of a heart and/or vessel function according to the present disclosure, the processor is operable to evaluate the maximum rate of volumetric change of the heart. In another embodiment, the processor is operable to evaluate the maximum rate of volumetric change of the heart. In yet another embodiment, the processor compares the conductance data from conductance acquired from the outer surface of a vessel.

In at least one embodiment of a system according to the present disclosure, the processor compares the conductance data from conductance acquired from the lumen surface of a vessel. In another embodiment, the processor compares the parallel conductance data from parallel conductance acquired from the outer surface of a vessel. In yet another embodiment, the processor compares the parallel conductance data from parallel conductance acquired from the lumen surface of a vessel.

In at least one embodiment of a system for determining the index of a heart and/or vessel function according to the present disclosure, the patch is positioned upon the epicardial surface of a vessel, and wherein the conductance reader is operable to detect conductance from the epicardial surface of the vessel. In another embodiment, the patch is positioned upon the lumen surface of a vessel, and wherein the conductance reader is operable to detect conductance from the lumen surface of the vessel. In yet another embodiment, the patch is positioned upon the epicardial surface of a vessel, and wherein the parallel conductance reader is operable to detect parallel conductance from the epicardial surface of the vessel.

In at least one embodiment of a system according to the present disclosure, the patch is positioned upon the lumen surface of a vessel, and wherein the parallel conductance reader is operable to detect parallel conductance from the lumen surface of the vessel. In an additional embodiment, the processor is operable to evaluate the maximum rate of lumen cross-sectional area change of a vessel. In yet an additional embodiment, the processor is operable to evaluate the maximum rate of lumen cross-sectional area change of a vessel.

In at least one embodiment of a system according to the present disclosure, the system further comprises a current source, the current source operable to provide a supply of electrical current to the first excitation electrode and the second excitation electrode to facilitate the detection of conductance from the first detection electrode and the second detection electrode. In another embodiment, the system further comprises a current source, the current source operable to provide a supply of electrical current to the first excitation electrode and the second excitation electrode to facilitate the detection of parallel conductance from the first detection electrode and the second detection electrode. In yet another embodiment, the first excitation electrode, the second excitation electrode, the first detection electrode, and the second detection electrode each comprise a wire, and wherein each wire is insulated from the other wires.

In at least one embodiment of a system for determining the index of a heart and/or vessel function according to the present disclosure, the system comprises an impedance catheter assembly, the impedance catheter assembly comprising a catheter, the catheter comprising a patch, the patch comprising a first excitation electrode, a second excitation electrode, a first detection electrode, and a second detection electrode, and a conductance reader in connection with the catheter assembly, the conductance reader operable to operable to detect conductance from the first detection electrode and the second detection electrode, wherein the conductance reader comprises a data acquisition and processing system comprising a processor, a storage medium operably connected to the processor, the storage medium capable of receiving and storing conductance data, and a program stored upon the storage medium, the program operable by the processor upon the conductance data to compare the conductance data to a rate of volumetric change of a heart and/or vessel, whereby an assessment of the index of a heart and/or vessel function may be determined based upon the conductance detected from the first detection electrode and the second detection electrode.

In at least one embodiment of a system for determining the index of a heart and/or vessel function according to the present disclosure, the system comprises an impedance catheter assembly, the impedance catheter assembly comprising a catheter, the catheter comprising a patch, the patch comprising a first excitation electrode, a second excitation electrode, a first detection electrode, and a second detection electrode, and a parallel conductance reader in connection with the catheter assembly, the parallel conductance reader operable to operable to detect parallel conductance from the first detection electrode and the second detection electrode, wherein the parallel conductance reader comprises a data acquisition and processing system comprising a processor, a storage medium operably connected to the processor, the storage medium capable of receiving and storing parallel conductance data, and a program stored upon the storage medium, the program operable by the processor upon the parallel conductance data to compare the parallel conductance data to a rate of volumetric change of a heart and/or vessel, whereby an assessment of the index of a heart and/or vessel function may be determined based upon the parallel conductance detected from the first detection electrode and the second detection electrode.

In at least one embodiment of a program having a plurality of program steps to be executed on a computer having a processor and a storage medium to analyze conductance data according to the present disclosure, the program is operable to receive conductance data from a conductance reader, and analyze the conductance data to determine the index of heart and/or vessel function. In another embodiment, the program is further operable to evaluate the maximum rate of volumetric change of the heart and/or vessel. In yet another embodiment, the program is further operable to evaluate the maximum rate of lumen cross-sectional area change of a vessel.

In at least one embodiment of a program having a plurality of program steps to be executed on a computer having a processor and a storage medium to analyze parallel conductance data according to the present disclosure, the program is operable to receive parallel conductance data from a parallel conductance reader, and analyze the parallel conductance data to determine the index of heart and/or vessel function. In an additional embodiment, the program is further operable to evaluate the maximum rate of volumetric change of the heart and/or vessel. In yet an additional embodiment, the program is further operable to evaluate the maximum rate of lumen cross-sectional area change of a vessel.

In at least one embodiment of a method of determining an index of heart function according to the present disclosure, the method comprises the steps of introducing an impedance catheter into a pericardial space on the surface of a heart, measuring a parallel conductance during a cardiac cycle, and generating an efficiency model of the heart from the parallel conductance. In another embodiment, the impedance catheter comprises a patch, the patch comprising a first excitation electrode, a second excitation electrode, a first detection electrode, and a second detection electrode. In yet another embodiment, the step of measuring a parallel conductance is performed by obtaining parallel conductance from the first detection electrode and the second detection electrode.

In at least one embodiment of a method of determining an index of heart function according to the present disclosure, the step of generating an efficiency model further comprises the step of comparing the parallel conductance to a rate of volumetric change of the heart. In another embodiment, the step of measuring a parallel conductance comprises multiple parallel conductance measurements to determine the volume of the heart. In yet another embodiment, the step of measuring a parallel conductance comprises the use of a parallel conductance reader operably coupled to the impedance catheter. In even another embodiment, the step of generating an efficiency model further comprises the step of evaluating the maximum rate of volumetric change of the heart.

In at least one embodiment of a method of determining an index of heart function according to the present disclosure, the method comprises the steps of introducing an impedance catheter into a pericardial space on the surface of a heart, measuring a general conductance during a cardiac cycle, and generating an efficiency model of the heart from the general conductance. In another embodiment, the impedance catheter comprises a patch, the patch comprising a first excitation electrode, a second excitation electrode, a first detection electrode, and a second detection electrode. In yet another embodiment, the step of measuring a general conductance is performed by obtaining general conductance from the first detection electrode and the second detection electrode. In a further embodiment, the step of generating an efficiency model further comprises the step of comparing the general conductance to a rate of volumetric change of the heart.

In at least one embodiment of a method of determining an index of heart function according to the present disclosure, the step of measuring a general conductance comprises multiple general conductance measurements to determine the volume of the heart. In another embodiment, the step of measuring a general conductance comprises the use of a general conductance reader operably coupled to the impedance catheter. In yet another embodiment, the step of generating an efficiency model further comprises the step of evaluating the maximum rate of volumetric change of the heart.

In at least one embodiment of a method of determining an index of heart function according to the present disclosure, the method comprises the steps of introducing an impedance catheter into a lumen of a heart measuring a parallel conductance during a cardiac cycle, and generating an efficiency model of the heart from the parallel conductance. In another embodiment, the impedance catheter comprises a patch, the patch comprising a first excitation electrode, a second excitation electrode, a first detection electrode, and a second detection electrode. In yet another embodiment, the step of measuring a parallel conductance is performed by obtaining parallel conductance from the first detection electrode and the second detection electrode.

In at least one embodiment of a method of determining an index of heart function according to the present disclosure, the step of generating an efficiency model further comprises the step of comparing the parallel conductance to a rate of volumetric change of the heart. In another embodiment, the step of measuring a parallel conductance comprises multiple parallel conductance measurements to determine the volume of the heart. In even another embodiment, the step of measuring a parallel conductance comprises the use of a parallel conductance reader operably coupled to the impedance catheter. In yet another embodiment, the step of generating an efficiency model further comprises the step of evaluating the maximum rate of volumetric change of the heart.

In at least one embodiment of a method of determining an index of heart function according to the present disclosure, the method comprises the steps of introducing an impedance catheter into a lumen of a heart, measuring a general conductance during a cardiac cycle, and generating an efficiency model of the heart from the general conductance. In an additional embodiment, the impedance catheter comprises a patch, the patch comprising a first excitation electrode, a second excitation electrode, a first detection electrode, and a second detection electrode. In yet an additional embodiment, the step of measuring a general conductance is performed by obtaining general conductance from the first detection electrode and the second detection electrode.

In at least one embodiment of a method of determining an index of heart function according to the present disclosure, the step of generating an efficiency model further comprises the step of comparing the general conductance to a rate of volumetric change of the heart. In another embodiment, the step of measuring a general conductance comprises multiple general conductance measurements to determine the volume of the heart. In yet another embodiment, the step of measuring a general conductance comprises the use of a general conductance reader operably coupled to the impedance catheter. In even another embodiment, the step of generating an efficiency model further comprises the step of evaluating the maximum rate of volumetric change of the heart.

In at least one embodiment of a method of determining an index of vessel function according to the present disclosure, the method comprises the steps of introducing an impedance catheter into a lumen of a vessel, measuring a parallel conductance during a cardiac cycle, and generating an efficiency model of the vessel from the parallel conductance. In another embodiment, the impedance catheter comprises a patch, the patch comprising a first excitation electrode, a second excitation electrode, a first detection electrode, and a second detection electrode. In yet another embodiment, the step of measuring a parallel conductance is performed by obtaining parallel conductance from the first detection electrode and the second detection electrode.

In at least one embodiment of a method of determining an index of vessel function according to the present disclosure, the step of generating an efficiency model further comprises the step of comparing the parallel conductance to a rate of volumetric change of the vessel. In an additional embodiment, the step of measuring a parallel conductance comprises a single parallel conductance measurement. In another embodiment, the step of measuring a parallel conductance comprises the use of a parallel conductance reader operably coupled to the impedance catheter. In yet another embodiment, the step of generating an efficiency model further comprises the step of evaluating the maximum rate of volumetric change of the vessel.

In at least one embodiment of a method of determining an index of vessel function according to the present disclosure, the method comprises the steps of introducing an impedance catheter into a lumen of a vessel; measuring a general conductance during a cardiac cycle, and generating an efficiency model of the vessel from the general conductance.

In another embodiment, the impedance catheter comprises a patch, the patch comprising a first excitation electrode, a second excitation electrode, a first detection electrode, and a second detection electrode. In yet another embodiment, the step of measuring a general conductance is performed by obtaining parallel conductance from the first detection electrode and the second detection electrode. In an additional embodiment, the step of generating an efficiency model further comprises the step of comparing the general conductance to a rate of volumetric change of the vessel.

In at least one embodiment of a method of determining an index of vessel function according to the present disclosure, the step of measuring a general conductance comprises a single general conductance measurement. In another embodiment, the step of measuring a general conductance comprises the use of a general conductance reader operably coupled to the impedance catheter. In yet another embodiment, the step of generating an efficiency model further comprises the step of evaluating the maximum rate of volumetric change of the vessel.

BRIEF DESCRIPTION OF THE DRAWINGS

FIG. 1A shows an embodiment of an engagement catheter and an embodiment of a delivery catheter as disclosed herein;

FIG. 1B shows a percutaneous intravascular pericardial delivery using another embodiment of an engagement catheter and another embodiment of a delivery catheter as disclosed herein;

FIG. 2A shows a percutaneous intravascular technique for accessing the pericardial space through a right atrial wall or atrial appendage using the engagement and delivery catheters shown in FIG. 1A;

FIG. 2B shows the embodiment of an engagement catheter shown in FIG. 2A;

FIG. 2C shows another view of the distal end of the engagement catheter embodiment shown in FIGS. 2A and 2B;

FIG. 3A shows removal of an embodiment of a catheter as disclosed herein;

FIG. 3B shows the resealing of a puncture according to an embodiment as disclosed herein;

FIGS. 4A, 4B, and 4C show a closure of a hole in the atrial wall using an embodiment as disclosed herein;

FIG. 5A shows an embodiment of an engagement catheter as disclosed herein;

FIG. 5B shows a cross-sectional view of the proximal end of the engagement catheter shown in FIG. 5A;

FIG. 5C shows a cross-sectional view of the distal end of the engagement catheter shown in FIG. 5A;

FIG. 6A shows an embodiment of a delivery catheter as disclosed herein;

FIG. 6B shows a close-up view of the needle shown in FIG. 6A;

FIG. 6C shows a cross-sectional view of the needle shown in FIGS. 6A and 6B;

DETAILED DESCRIPTION

Figure 5D:
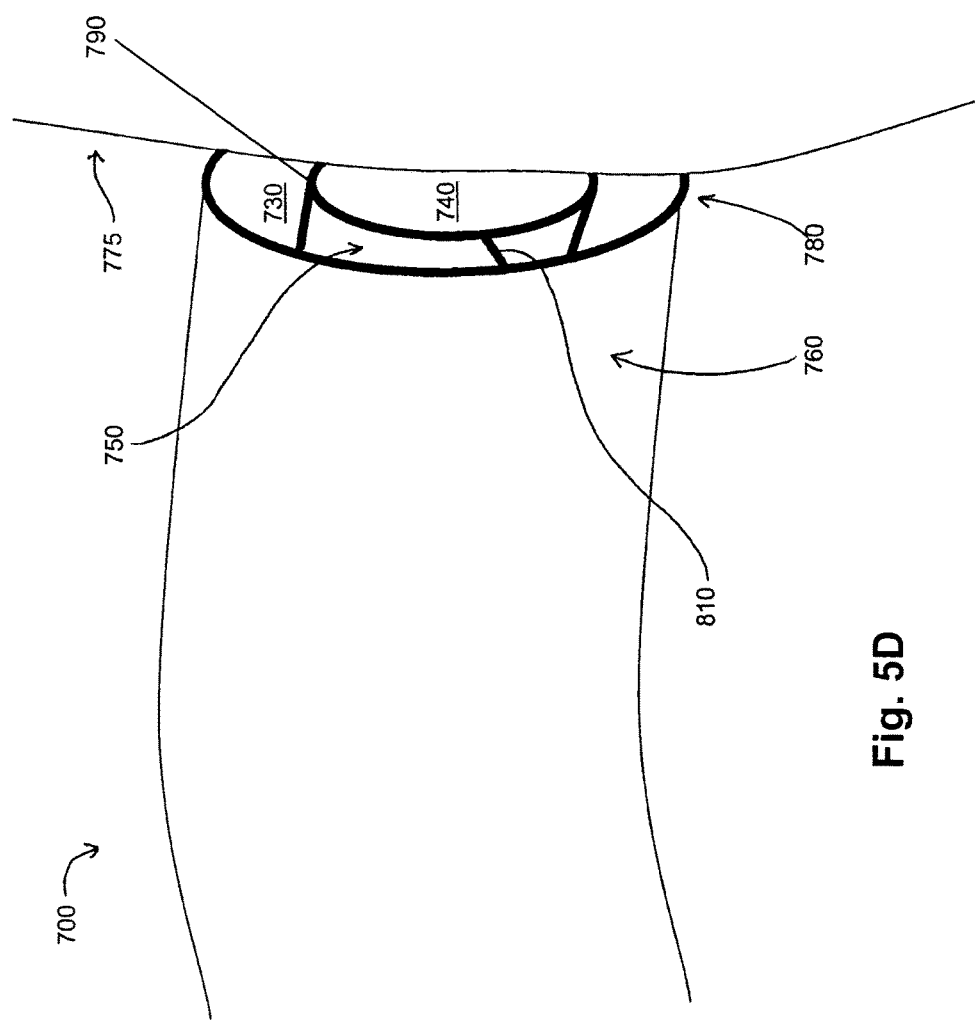
FIG. 5D shows the engagement catheter shown in FIG. 5A approaching a heart wall from inside of the heart.

The disclosure of the present application measures an index of vessel and heart function to evaluate the efficiency of the cardiovascular system and risk of disease. For the purposes of promoting an understanding of the principles of the present disclosure, reference will now be made to the embodiments illustrated in the drawings, and specific language will be used to describe the same. It will nevertheless be understood that no limitation of the scope of the present disclosure is thereby intended.

Vessel Contractility

Regarding vessel contractility, an assumption is made that an artery as a thick-walled cylindrical shell consisting of incompressible, homogeneous, isotropic, elastic material. The inner and outer radii of the shell are denoted by $r_i$ and $r_e$, respectively. The outer surface is considered load-free white the inner surface is subjected to blood pressure P(t), where t is time. The circumferential wall stress ($\sigma_\theta$) can be expressed at any transmural radial position in the wall, r, as Lame's formula:

$$\sigma_\theta = P\left[\frac{(r_e^2/r_i^2)+1}{(r_e^2/r_i^2)-1}\right] \qquad \text{[Equation \#1]}$$

The maximum wall stress occurs at the intima, and is given by:

$$\sigma_\theta(ri) = P\left[\frac{(r_e^2/r_i^2)+1}{(r_e^2/r_i^2)-1}\right] \qquad \text{[Equation \#2]}$$

The geometric relation between vessel wall volume ($V_w$), vessel cavity volume (V), $r_i$ and $r_e$ can be expressed as:

$$V_w = \pi(r_e^2 - r_i^2)L \text{ and } V = \pi r_i^2 L \qquad \text{[Equation \#3]}$$

where L is the length of the vessel. If we combine Equation #2 and Equation #3, the following desired result is obtained:

$$\sigma_\theta = P\left[\frac{2V}{V_w}+1\right] \qquad \text{[Equation \#4]}$$

By normalizing wall stress to blood pressure (P), an index of LV contractile function may result as:

$$\sigma_\theta/P = \frac{2V}{V_w}+1 \qquad \text{[Equation \#5]}$$

Analogous to $dP/dt_{max}$, we propose a vessel contractility index as the maximal rate of change of pressure-normalized wall stress; i.e., namely:

$$d\sigma^*/dt_{max} = \frac{d(\sigma_\theta/P)}{dt}\bigg|_{max} = \frac{2}{V_w}\frac{dV}{dt}\bigg|_{max} \qquad \text{[Equation \#6]}$$

Since the length of the vessel remains constant, Equation #6 can be written in terms of lumen area, CSA, as:

$$d\sigma^*/dt_{max} = \frac{2}{V_w L}\frac{dCSA}{dt}\bigg|_{max} \qquad \text{[Equation \#7]}$$

As such, the maximum rate of change of the vessel lumen cross-sectional area is an important index of contractility, and hence, vascular function.

Conventional clinical imaging (magnetic resonance imaging (MRI), computed tomography (CT), ultrasound (US), etc.) can be used in conjunction with Equation #7 to yield an index of vessel function of a patient. This index can be determined under resting conditions during the cardiac cycle, after a cuff occlusion to specifically examine endothelial function, or after a pharmacological challenge to evaluate the vasoactive tone of vessel.

Cardiac Contractility

The formulation as described above may also be used to evaluate heart function. The disclosure of the present application reveals that a similar equation (Equation #6) results if a cylinder or a spherical geometry is assumed but with a different proportionality constant. Hence, a similar strategy of combining current non-invasive imaging (CT, MRI, US, etc.) with Equation #6 to yield a patient specific contractility index.

Contractility Index Based on Electrical Impedance Vessel

As referenced by prior studies, the conductance of current flow through the organ lumen and organ wall and surrounding tissue is parallel. For example, $$G(z, t) = \frac{CSA(z, t) \cdot C_b}{L} + G_p(z, t) \qquad \text{[Equation \#8]}$$

where $G_p(z,t)$ is the effective conductance of the structure outside the bodily fluid (organ wall and surrounding tissue), $C_b$ is the specific electrical conductivity of the bodily fluid, CSA is the lumen cross-sectional area of the organ and L is the distance between the detection electrodes. This concept was previously used to determine luminal area. However, the disclosure of the present application identifies that the same concept can be applied here for blood vessels with the use of Equation #7 to determine the function of blood vessels during percutaneous catheterization. Since only the change of CSA is required, Equation #8 can be reduced to:

$$\frac{dCSA}{dt}\bigg|_{max} = \frac{dG}{dt}\bigg|_{max} \qquad \text{[Equation \#9]}$$

As such, the change of conductance is desired which does not require injections as referenced by earlier studies, and can be directly determined from the change of conductance.

Heart

Intra-Ventricle Approach

In previous studies, the catheter was placed inside of the lumen to determine the dimensional changes. This procedure can still be done for the heart with multiple leads (two outer excitation electrodes (E) but multiple sets of inner detection electrodes (D)) to add up the cross-sectional areas to provide the volume, and hence, Equation #6. Again, only the change in conductance is required which does not necessitate any saline injections.

Epicardial Approach

Previous studies introduced the ability to introduce a catheter in the pericardial space on the surface of the heart. Such techniques include devices, systems, and methods useful for accessing various tissues of the heart from inside the heart. For example, various embodiments provide for percutaneous, intravascular access into the pericardial space through an atrial wall or the wall of an atrial appendage. In at least some embodiments, the heart wall is aspirated and retracted from the pericardial sac to increase the pericardial space between the heart and the sac and thereby facilitate access into the space.

Unlike the relatively stiff pericardial sac, the atrial wall and atrial appendage are rather soft and deformable. Hence, suction of the atrial wall or atrial appendage can provide significantly more clearance of the cardiac structure from the pericardium as compared to suction of the pericardium. Furthermore, navigation from the intravascular region (inside of the heart) provides more certainty of position of vital cardiac structures than does intrathoracic access (outside of the heart).

Access to the pericardial space may be used for identification of diagnostic markers in the pericardial fluid; for pericardiocentesis; and for administration of therapeutic factors with angiogenic, myogenic, and antiarrhythmic potential. In addition, epicardial pacing leads may be delivered via the pericardial space, and an ablation catheter may be used on the epicardial tissue from the pericardial space.

In the embodiment of the catheter system shown in FIG. 1A, catheter system 10 includes an engagement catheter 20, a delivery catheter 30, and a needle 40. Although each of engagement catheter 20, delivery catheter 30, and needle 40 has a proximal end and a distal end, FIG. 1A shows only the distal end. Engagement catheter 20 has a lumen through which delivery catheter 30 has been inserted, and delivery catheter 30 has a lumen through which needle 40 has been inserted. Delivery catheter 30 also has a number of openings 50 that can be used to transmit fluid from the lumen of the catheter to the heart tissue in close proximity to the distal end of the catheter. It can be appreciated that catheter system 10, engagement catheter 20, and delivery catheter 30 may be generally referred to as a "catheter."

As shown in more detail in FIGS. 2A, 2B, and 2C, engagement catheter 20 includes a vacuum channel 60 used for suction of a targeted tissue 65 in the heart and an injection channel 70 used for infusion of substances to targeted tissue 65, including, for example, a biological or non-biological degradable adhesive. As is shown in FIGS. 2B and 2C, injection channel 70 is ring-shaped, which tends to provide relatively even dispersal of the infused substance over the targeted tissue, but other shapes of injection channels may be suitable. A syringe 80 is attached to injection channel 70 for delivery of the appropriate substances to injection channel 70, and a syringe 90 is attached to vacuum channel 60 through a vacuum port (not shown) at the proximal end of engagement catheter 20 to provide appropriate suction through vacuum channel 60. At the distal end of engagement catheter 20, a suction port 95 is attached to vacuum channel 60 for contacting targeted tissue 65, such that suction port 95 surrounds targeted tissue 65, which is thereby encompassed within the circumference of suction port 95. Although syringe 90 is shown in FIG. 2B as the vacuum source providing suction for engagement catheter 20, other types of vacuum sources may be used, such as a controlled vacuum system providing specific suction pressures. Similarly, syringe 80 serves as the external fluid source in the embodiment shown in FIG. 2B, but other external fluid sources may be used.

A route of entry for use of various embodiments disclosed herein is through the jugular or femoral vein to the superior or inferior vena cavae, respectively, to the right atrial wall or atrial appendage (percutaneously) to the pericardial sac (through puncture).

Referring now to FIG. 1B, an engagement catheter 100 is placed via standard approach into the jugular or femoral vein. The catheter, which may be 4 or 5 Fr., is positioned under fluoroscopic or echocardiographic guidance into the right atrial appendage 110. Suction is initiated to aspirate a portion of atrial appendage 110 away from the pericardial sac 120 that surrounds the heart. As explained herein, aspiration of the heart tissue is evidenced when no blood can be pulled back through engagement catheter 100 and, if suction pressure is being measured, when the suction pressure gradually increases. A delivery catheter 130 is then inserted through a lumen of engagement catheter 100. A small perforation can be made in the aspirated atrial appendage 110 with a needle such as needle 40, as shown in FIGS. 1A and 2A. A guide wire (not shown) can then be advanced through delivery catheter 130 into the pericardial space to secure the point of entry 125 through the atrial appendage and guide further insertion of delivery catheter 130 or another catheter. Flouroscopy or echocardiogram can be used to confirm the position of the catheter in the pericardial space. Alternatively, a pressure tip needle can sense the pressure and measure the pressure change from the atrium (about 10 mmHg) to the pericardial space (about 2 mmHg). This is particularly helpful for transeptal access where puncture of arterial structures (e.g., the aorta) can be diagnosed and sealed with an adhesive, as described in more detail below.

Although aspiration of the atrial wall or the atrial appendage retracts the wall or appendage from the pericardial sac to create additional pericardial space, $CO_2$ gas can be delivered through a catheter, such as delivery catheter 130, into the pericardial space to create additional space between the pericardial sac and the heart surface.

Referring now to FIG. 3A, the catheter system shown in FIG. 1B is retrieved by pull back through the route of entry. However, the puncture of the targeted tissue in the heart (e.g., the right atrial appendage as shown in FIG. 3A) may be sealed upon withdrawal of the catheter, which prevents bleeding into the pericardial space. The retrieval of the catheter may be combined with a sealing of the tissue in one of several ways: (1) release of a tissue adhesive or polymer 75 via injection channel 70 to seal off the puncture hole, as shown in FIG. 3B; (2) release of an inner clip or mechanical stitch to close off the hole from the inside of the cavity; or (3) mechanical closure of the heart with a sandwich type mechanical device that approaches the hole from both sides of the wall (see FIGS. 4A, 4B, and 4C). In other words, closure may be accomplished by using, for example, a biodegradable adhesive material (e.g., fibrin glue or cyanomethacrylate), a magnetic system, or an umbrella-shaped nitinol stent. An example of the closure of a hole in the atrium is shown in FIG. 3B. Engagement catheter 20 is attached to targeted tissue 95 using suction through suction port 60. Tissue adhesive 75 is injected through injection channel 70 to coat and seal the puncture wound in targeted tissue 95. Engagement catheter 20 is then withdrawn, leaving a plug of tissue adhesive 75 attached to the atrial wall or atrial appendage.

Another example for sealing the puncture wound in the atrial wall or appendage is shown in FIGS. 4A, 4B, and 4C. A sandwich-type closure, having an external cover 610 and an internal cover 620, is inserted through the lumen of engagement catheter 600, which is attached to the targeted tissue of an atrial wall 630. Each of external and internal covers 610 and 620 is similar to an umbrella in that it can be inserted through a catheter in its folded configuration and expanded once it is outside of the catheter. As shown in FIG. 4A, external cover 610 is deployed (in its expanded configuration) on the outside of the atrial wall to seal a puncture wound in the targeted tissue. Internal cover 620 is delivered through engagement catheter 600 (in its folded configuration), as shown in FIGS. 4A and 4B. Once internal cover 620 is in position on the inside of atrial wall 630 at the targeted tissue, internal cover 620 is deployed to help seal the puncture wound in the targeted tissue (see FIG. 4C). Engagement catheter 600 then releases its grip on the targeted tissue and is withdrawn, leaving the sandwich-type closure to seal the puncture wound, as shown in FIG. 4C. External cover 610 and internal cover 620 may be held in place using adhesion or magnetic forces.

FIGS. 5A, 5B, 5C, and 5D show another embodiment of an engagement catheter as disclosed herein. Engagement catheter 700 is an elongated tube having a proximal end 710 and a distal end 720, as well as two lumens 730, 740 extending between proximal end 710 and distal end 720. Lumens 730, 740 are formed by concentric inner wall 750 and outer wall 760, as particularly shown in FIGS. 5B and 5C. At proximal end 710, engagement catheter 700 includes a vacuum port 770, which is attached to lumen 730 so that a vacuum source can be attached to vacuum port 770 to create suction in lumen 730, thereby forming a suction channel. At distal end 720 of catheter 700, a suction port 780 is attached to lumen 730 so that suction port 780 can be placed in contact with heart tissue 775 (see FIG. 5D) for aspirating the tissue, thereby forming a vacuum seal between suction port 780 and tissue 775 when the vacuum source is attached and engaged. The vacuum seal enables suction port 780 to grip, stabilize, and retract tissue 775. For example, attaching a suction port to an interior atrial wall using a vacuum source enables the suction port to retract the atrial wall from the pericardial sac surrounding the heart, which enlarges the pericardial space between the atrial wall and the pericardial sac.

As shown in FIG. 5C, two internal lumen supports 810, 820 are located within lumen 730 and are attached to inner wall 750 and outer wall 760 to provide support to the walls. These lumen supports divide lumen 730 into two suction channels. Although internal lumen supports 810, 820 extend from distal end 720 of catheter 700 along a substantial portion of the length of catheter 700, internal lumen supports 810, 820 may or may not span the entire length of catheter 700. Indeed, as shown in FIGS. 5A, 5B, and 5C, internal lumen supports 810, 820 do not extend to proximal end 710 to ensure that the suction from the external vacuum source is distributed relatively evenly around the circumference of catheter 700. Although the embodiment shown in FIG. 5C includes two internal lumen supports, other embodiments may have just one internal support or even three or more such supports.

FIG. 5D shows engagement catheter 700 approaching heart tissue 775 for attachment thereto. It is important for the clinician performing the procedure to know when the suction port has engaged the tissue of the atrial wall or the atrial appendage. For example, in reference to FIG. 5D, it is clear that suction port 780 has not fully engaged tissue 775 such that a seal is formed. However, because suction port 780 is not usually seen during the procedure, the clinician may determine when the proper vacuum seal between the atrial tissue and the suction port has been made by monitoring the amount of blood that is aspirated, by monitoring the suction pressure with a pressure sensor/regulator, or both. For example, as engagement catheter 700 approaches the atrial wall tissue (such as tissue 775) and is approximately in position, the suction can be activated through lumen 730. A certain level of suction (e.g., 10 mmHg) can be imposed and measured with a pressure sensor/regulator. As long as catheter 700 does not engage the wall, some blood will be aspirated into the catheter and the suction pressure will remain the same. However, when catheter 700 engages or attaches to the wall of the heart (depicted as tissue 775 in FIG. 5D), minimal blood is aspirated and the suction pressure will start to gradually increase. Each of these signs can alert the clinician (through alarm or other means) as an indication of engagement. The pressure regulator is then able to maintain the suction pressure at a preset value to prevent over-suction of the tissue.

An engagement catheter, such as engagement catheter 700, may be configured to deliver a fluid or other substance to tissue on the inside of a wall of the heart, including an atrial wall or a ventricle wall. For example, lumen 740 shown in FIGS. 5A and 5C includes an injection channel 790 at distal end 720. Injection channel 790 dispenses to the targeted tissue a substance flowing through lumen 740. As shown in FIG. 5D, injection channel 790 is the distal end of lumen 740. However, in other embodiments, the injection channel may be ring-shaped (see FIG. 2C) or have some other suitable configuration.

Substances that can be locally administered with an engagement catheter include preparations for gene or cell therapy, drugs, and adhesives that are safe for use in the heart. The proximal end of lumen 740 has a fluid port 800, which is capable of attachment to an external fluid source for supply of the fluid to be delivered to the targeted tissue. Indeed, after withdrawal of a needle from the targeted tissue, as discussed herein, an adhesive may be administered to the targeted tissue by the engagement catheter for sealing the puncture wound left by the needle withdrawn from the targeted tissue.

Referring now to FIGS. 6A, 6B, and 6C, there is shown a delivery catheter 850 comprising an elongated hollow tube 880 having a proximal end 860, a distal end 870, and a lumen 885 along the length of the catheter. Extending from distal end 870 is a hollow needle 890 in communication with lumen 885. Needle 890 is attached to distal end 870 in the embodiment of FIGS. 6A, 6B, and 6C, but, in other embodiments, the needle may be removably attached to, or otherwise located at, the distal end of the catheter (see FIG. 1A). In the embodiment shown in FIGS. 6A, 6B, and 6C, as in certain other embodiments having an attached needle, the junction (i.e., site of attachment) between hollow tube 880 and needle 890 forms a security notch 910 circumferentially around needle 890 to prevent needle 890 from over-perforation. Thus, when a clinician inserts needle 890 through an atrial wall to gain access to the pericardial space, the clinician will not, under normal conditions, unintentionally perforate the pericardial sac with needle 890 because the larger diameter of hollow tube 880 (as compared to that of needle 890) at security notch 910 hinders further needle insertion. Although security notch 910 is formed by the junction of hollow tube 880 and needle 890 in the embodiment shown in FIGS. 6A, 6B, and 6C, other embodiments may have a security notch that is configured differently. For example, a security notch may include a band, ring, or similar device that is attached to the needle a suitable distance from the tip of the needle. Like security notch 910, other security notch embodiments hinder insertion of the needle past the notch itself by presenting a larger profile than the profile of the needle such that the notch does not easily enter the hole in the tissue caused by entry of the needle.

It is useful for the clinician performing the procedure to know when the needle has punctured the atrial tissue. This can be done in several ways. For example, the delivery catheter can be connected to a pressure transducer to measure pressure at the tip of the needle. Because the pressure is lower and much less pulsatile in the pericardial space than in the atrium, the clinician can recognize immediately when the needle passes through the atrial tissue into the pericardial space.

Alternatively, as shown in FIG. 6B, needle 890 may be connected to a strain gauge 915 as part of the catheter assembly. When needle 890 contacts tissue (not shown), needle 890 will be deformed. The deformation will be transmitted to strain gauge 915 and an electrical signal will reflect the deformation (through a classical wheatstone bridge), thereby alerting the clinician. Such confirmation of the puncture of the wall can prevent over-puncture and can provide additional control of the procedure.

In some embodiments, a delivery catheter, such as catheter 850 shown in FIGS. 6A, 6B, and 6C, is used with an engagement catheter, such as catheter 700 shown in FIGS. 5A, 5B, 5C, and 5D, to gain access to the pericardial space between the heart wall and the pericardial sac. For example, engagement catheter 700 may be inserted into the vascular system and advanced such that the distal end of the engagement catheter is within the atrium. The engagement catheter may be attached to the targeted tissue on the interior of a wall of the atrium using a suction port as disclosed herein. A standard guide wire may be inserted through the lumen of the delivery catheter as the delivery catheter is inserted through the inner lumen of the engagement catheter, such as lumen 740 shown in FIGS. 5B and 5C. Use of the guide wire enables more effective navigation of the delivery catheter 850 and prevents the needle 890 from damaging the inner wall 750 of the engagement catheter 700. When the tip of the delivery catheter with the protruding guide wire reaches the atrium, the wire is pulled back, and the needle is pushed forward to perforate the targeted tissue. The guide wire is then advanced through the perforation into the pericardial space, providing access to the pericardial space through the atrial wall.

Referring again to FIGS. 6A, 6B, and 6C, lumen 885 of delivery catheter 850 may be used for delivering fluid into the pericardial space after needle 890 is inserted through the atrial wall or the atrial appendage. After puncture of the wall or appendage, a guide wire (not shown) may be inserted through needle lumen 900 into the pericardial space to maintain access through the atrial wall or appendage. Fluid may then be introduced to the pericardial space in a number of ways. For example, after the needle punctures the atrial wall or appendage, the needle is generally withdrawn. If the needle is permanently attached to the delivery catheter, as in the embodiment shown in FIGS. 6A and 6B, then delivery catheter 850 would be withdrawn and another delivery catheter (without an attached needle) would be introduced over the guide wire into the pericardial space. Fluid may then be introduced into the pericardial space through the lumen of the second delivery catheter.

In some embodiments, however, only a single delivery catheter is used. In such embodiments, the needle is not attached to the delivery catheter, but instead may be a needle wire (see FIG. 1A). In such embodiments, the needle is withdrawn through the lumen of the delivery catheter, and the delivery catheter may be inserted over the guide wire into the pericardial space. Fluid is then introduced into the pericardial space through the lumen of the delivery catheter.

The various embodiments disclosed herein may be used by clinicians, for example: (1) to deliver genes, cells, drugs, etc.; (2) to provide catheter access for epicardial stimulation; (3) to evacuate fluids acutely (e.g., in cases of pericardial tampondae) or chronically (e.g., to alleviate effusion caused by chronic renal disease, cancer, etc.); (4) to perform transseptal puncture and delivery of a catheter through the left atrial appendage for electrophysiological therapy, biopsy, etc.; (5) to deliver a magnetic glue or ring through the right atrial appendage to the aortic root to hold a percutaneous aortic valve in place; (6) to deliver a catheter for tissue ablation, e.g., to the pulmonary veins, or right atrial and epicardial surface of the heart for atrial and ventricular arrythmias; (7) to deliver and place epicardial, right atrial, and right and left ventricle pacing leads; (8) to occlude the left atrial appendage through percutaneous approach; and (9) to visualize the pericardial space with endo-camera or scope to navigate the epicardial surface of the heart for therapeutic delivery, diagnosis, lead placement, mapping, etc. Many other applications, not explicitly listed here, are also possible and within the scope of the present disclosure.

Figure 7:
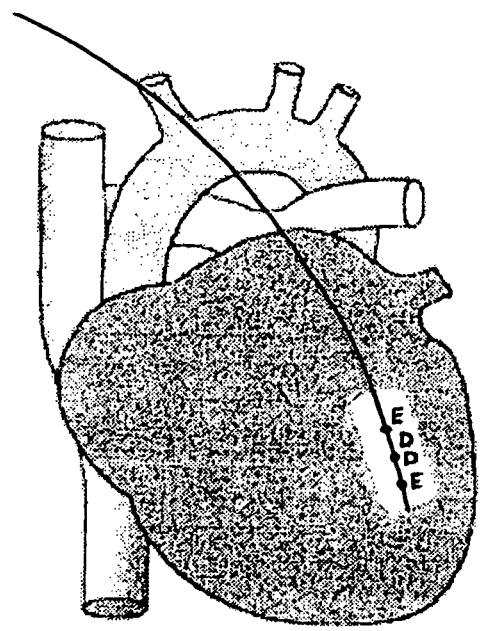
FIG. 7 shows an impedance catheter according to at least one embodiment of the present disclosure placed on the surface of the heart.

If an impedance catheter is placed on the surface of the heart as shown in FIG. 7, the parallel conductance (Gp) will change during the cardiac cycle. Since the first term in Equation #8 will not change significantly, then:

$$\left.\frac{dG}{dt}\right|_{max} = \left.\frac{dG_p}{dt}\right|_{max} \quad \text{[Equation \#10]}$$

Figure 8:
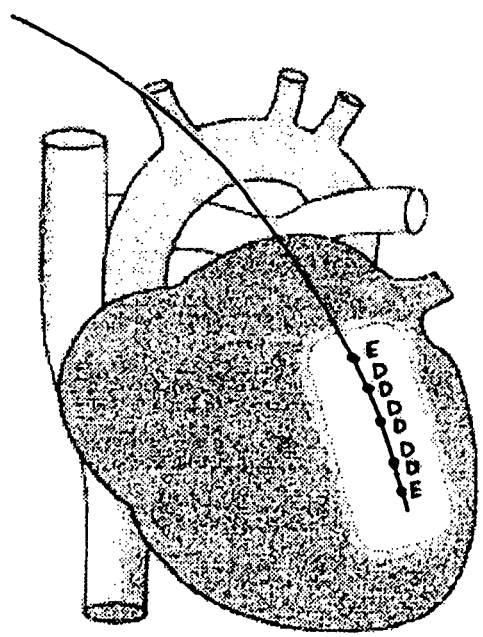
FIG. 8 shows an impedance catheter with multiple sets of detection leads according to at least one embodiment of the present disclosure placed on the surface of the heart.

Since Gp is proportional to the cross-sectional area, Equation #10 will yield the change of cross-sectional area. If an impedance catheter with multiple sets of detection leads is used as shown in FIG. 8, the desired rate of change of volume evaluate at the maximum point will be determined as an index of heart function.

Figure 9:
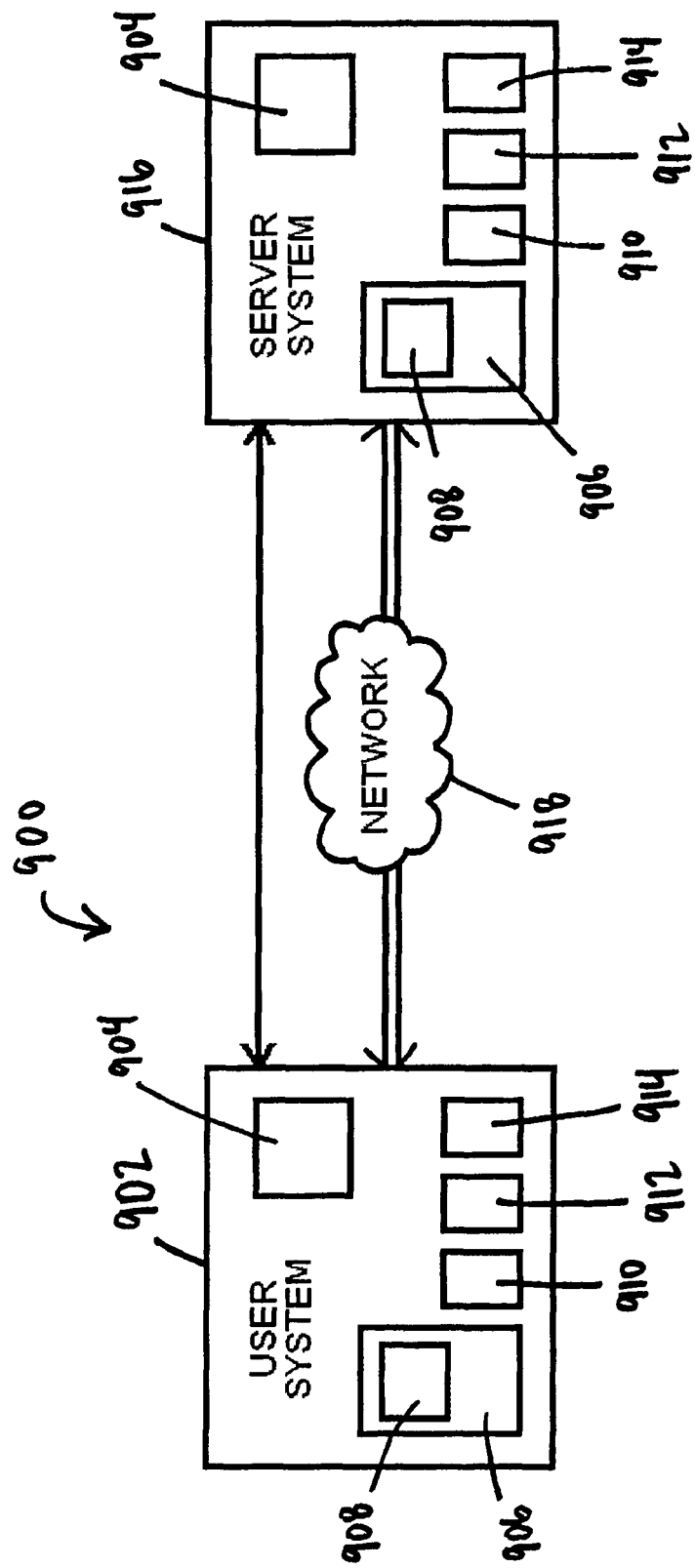
FIG. 9 shows a data acquisition and processing system according to at least one embodiment of the present disclosure.

Referring now to FIG. 9, there is shown a diagrammatic view of an embodiment of data acquisition and processing system 900 of the present disclosure. In the embodiment shown in FIG. 9, data acquisition and processing system 900 comprises user system 902. In this exemplary embodiment, user system 902 comprises processor 904 and one or more storage media 906. Processor 904 operates upon data obtained by or contained within user system 902. Storage medium 906 may contain database 908, whereby database 908 is capable of storing and retrieving data. Storage media 906 may contain a program (including, but not limited to, database 908), the program operable by processor 904 to perform a series of steps regarding conductance data as described in further detail herein. By way of example, the program may be operable by processor 904 to analyze conductance data, including analysis of such data in accordance with Equations #1-10 as described herein.

Any number of storage media 906 may be used with data acquisition and processing system 900 of the present disclosure, including, but not limited to, one or more of random access memory, read only memory, EPROMs, hard disk drives, floppy disk drives, optical disk drives, cartridge media, and smart cards, for example. As related to user system 902, storage media 906 may operate by storing conductance data for access by a user and/or for storing computer instructions. Processor 904 may also operate upon data stored within database 908.

Regardless of the embodiment of data acquisition and processing system 900 referenced herein and/or contemplated to be within the scope of the present disclosure, each user system 902 may be of various configurations well known in the art. By way of example, user system 902, as shown in FIG. 9, comprises keyboard 910, monitor 912, and printer 914. Processor 904 may further operate to manage input and output from keyboard 910, monitor 912, and printer 914. Keyboard 910 is an exemplary input device, operating as a means for a user to input information to user system 902. Monitor 912 operates as a visual display means to display the conductance data and related information to a user using a user system 902. Printer 914 operates as a means to display conductance data and related information. Other input and output devices, such as a keypad, a computer mouse, a fingerprint reader, a pointing device, a microphone, and one or more loudspeakers are contemplated to be within the scope of the present disclosure. It can be appreciated that processor 904, keyboard 910, monitor 912, printer 914 and other input and output devices referenced herein may be components of one or more user systems 902 of the present disclosure.

It can be appreciated that data acquisition and processing system 900 may further comprise one or more server systems 916 in bidirectional communication with user system 902, either by direct communication (shown by the single line connection on FIG. 9), or through a network 918 (shown by the double line connections on FIG. 9) by one of several configurations known in the art. Such server systems 916 may comprise one or more of the features of a user system 902 as described herein, including, but not limited to, processor 904, storage media 906, database 908, keyboard 910, monitor 912, and printer 914, as shown in the embodiment of data acquisition and processing system 900 shown in FIG. 9. Such server systems 916 may allow bidirectional communication with one or more user systems 902 to allow user system 902 to access conductance data and related information from the server systems 916. It can be appreciated that a user system 902 and/or a server system 916 referenced herein may be generally referred to as a "computer."

The catheter can be inserted into the pericardial space, as outlined in previous studies, or directly placed on as during open heart surgery. The patch containing the excitation electrodes (E) and detection electrodes (D) can be made to adhere to the surface through glue that is introduced through the lumen of the catheter into pores of the patch if the percutaneous approach is used. Alternatively, the patch may be glued on by hand with the open surgery approach. The electrodes are then interfaced with an impedance module to measure voltage differences as noted in prior studies.

The foregoing disclosure of the exemplary embodiments of the present application has been presented for purposes of illustration and description and can be further modified within the scope and spirit of this disclosure. It is not intended to be exhaustive or to limit the present disclosure to the precise forms disclosed. This application is therefore intended to cover any variations, uses, or adaptations of a device, system and method of the present application using its general principles. Further, this application is intended to cover such departures from the present disclosure as may come within known or customary practice in the art to which this system of the present application pertains. Many variations and modifications of the embodiments described herein will be apparent to one of ordinary skill in the art in light of the above disclosure. The scope of the present disclosure is to be defined only by the claims appended hereto, and by their equivalents.

Further, in describing representative embodiments of the present disclosure, the specification may have presented the method and/or process of the present disclosure as a particular sequence of steps. However, to the extent that the method or process does not rely on the particular order of steps set forth herein, the method or process should not be 'limited' to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present disclosure should not be limited to the performance of their steps in the order written, and one skilled in the art can readily appreciate that the sequences may be varied and still remain within the spirit and scope of the present disclosure.

What is claimed is:

1. A device for determining the index of a heart and/or vessel function, the device comprising:
    an impedance device comprising a first excitation electrode, a second excitation electrode, a first detection electrode, and a second detection electrode, the impedance device configured for percutaneous intravascular delivery and at least partial placement within a pericardial space and operable to obtain conductance data to determine at least one total conductance measurement when placed therein, the at least one total conductance measurement indicative of conductance of a heart wall, conductance of a ventricle adjacent to the heart wall, and conductance within the pericardial space, wherein the at least one total conductance measurement is obtained from within the pericardial space and without a determination of parallel conductance; and
    a conductance reader, the conductance reader in connection with the impedance device and operable to calculate the at least one total conductance measurement using the conductance data obtained from the first detection electrode and the second detection electrode and a max rate of change of a cross sectional area of the heart and/or vessel based on the calculated at least one total conductance measurement;
    whereby the max rate of change of the cross sectional area is sufficient to assess an index of a heart and/or vessel function without the determination of parallel conductance.

2. The device of claim 1, wherein the conductance reader comprises a data acquisition and processing system, the data acquisition and processing system comprising:
    a processor;
    a storage medium operably connected to the processor, the storage medium capable of receiving and storing the conductance data; and a program stored upon the storage medium, the program operable by the processor upon the conductance data to compare the conductance data to a rate of volumetric change of a heart and/or vessel.

3. The device of claim 2, wherein the processor is operable to compare the conductance data from conductance acquired from an epicardial surface of a heart.

4. The device of claim 2, wherein the processor is operable to compare the conductance data from conductance acquired from a lumen surface of a heart.

5. The device of claim 2, wherein the processor is operable to evaluate the maximum rate of volumetric change of the heart.

6. The device of claim 2, wherein the processor compares the conductance data from conductance acquired from the outer surface of a vessel.

7. The device of claim 2, wherein the processor compares the conductance data from conductance acquired from the lumen surface of a vessel.

8. The device of claim 2, wherein the device is configured to be positioned upon an epicardial surface of a vessel, and wherein the conductance reader is operable to detect conductance from the epicardial surface of the vessel.

9. The device of claim 2, wherein the device is configured to be positioned upon a lumen surface of a vessel, and wherein the conductance reader is operable to detect conductance from the lumen surface of the vessel.

10. The device of claim 2, wherein the processor is operable to evaluate the maximum rate of lumen cross-sectional area change of a vessel.

11. The device of claim 1, wherein the device is configured to be positioned upon an epicardial surface of a heart, and wherein the conductance reader is operable to detect conductance from the epicardial surface of the heart.

12. The device of claim 1, wherein the device is configured to be positioned upon a lumen surface of a heart, and wherein the conductance reader is operable to detect conductance from the lumen surface of the heart.

13. The device of claim 1, further comprising a current source, the current source operable to provide a supply of electrical current to the first excitation electrode and the second excitation electrode to facilitate the detection of conductance from the first detection electrode and the second detection electrode.

14. The device of claim 1, wherein the first excitation electrode, the second excitation electrode, the first detection electrode, and the second detection electrode each comprise a wire, and wherein each wire is insulated from the other wires.

15. A system for determining the index of a heart and/or vessel function the system comprising:
   an impedance assembly, the impedance assembly comprising a device comprising a first excitation electrode, a second excitation electrode, a first detection electrode, and a second detection electrode, the device configured for percutaneous intravascular delivery and at least partial placement within a pericardial space and operable to obtain conductance data to determine at least one total conductance measurement when placed therein, the at least one total conductance measurement indicative of conductance of a heart wall, conductance of a ventricle adjacent to the heart wall, and conductance within the pericardial space, wherein the at least one total conductance measurement is obtained from within the pericardial space and without a determination of parallel conductance; and
   a conductance reader in connection with the impedance assembly, the conductance reader operable to calculate the at least one total conductance measurement using the conductance data obtained from the first detection electrode and the second detection electrode and a max rate of change of a cross sectional area of the heart and/or vessel based on the calculated at least one total conductance measurement;
   whereby the max rate of change of the cross sectional area is sufficient to assess an index of a heart and/or vessel function without the determination of parallel conductance.

16. The system of claim 15, wherein the conductance reader comprises a data acquisition and processing system, the data acquisition and processing system comprising:
   a processor;
   a storage medium operably connected to the processor, the storage medium capable of receiving and storing conductance data; and
   a program stored upon the storage medium, the program operable by the processor upon the conductance data to compare the conductance data to a rate of volumetric change of a heart and/or vessel.

17. A non-transitory storage medium having a program stored thereon that, when executed by a processor, executes a plurality of program steps that are operable to:
   receive the total conductance data from a conductance reader, the conductance reader in communication with an impedance device;
   analyze the total conductance data to calculate a max rate of change of a cross sectional area of the heart and/or vessel and determine the index of heart and/or vessel function based on the max rate of change of the cross sectional area without a determination of parallel conductance data, wherein the total conductance data comprises at least one total conductance measurement obtained from within a pericardial space and without a determination of parallel conductance; and
   evaluate the maximum rate of volumetric change of the heart and/or vessel.

* * * * *